(12) United States Patent
Abo (10) Patent No.: US 7,261,560 B2
(45) Date of Patent: Aug. 28, 2007

(54) DENTAL SUCTION DEVICE

(75) Inventor: Takeshi Abo, Osaka (JP)

(73) Assignees: Shinya ABO, Osaka (JP); Hirokazu ABO, Hyogo (JP)

( * ) Notice: Subject to any disclaimer, the term of this patent is extended or adjusted under 35 U.S.C. 154(b) by 0 days.

(21) Appl. No.: 10/999,008

(22) Filed: Nov. 30, 2004

(65) Prior Publication Data

US 2006/0008764 A1    Jan. 12, 2006

(30) Foreign Application Priority Data

Jul. 12, 2004    (JP)    ............... 2004-205086

(51) Int. Cl.
*A61C 17/06*    (2006.01)

(52) U.S. Cl. ............... 433/95; 433/91; 433/93; 433/94; 433/96

(58) Field of Classification Search ............... 433/80, 433/91, 95, 96, 93, 94; 604/36, 128
See application file for complete search history.

(56) References Cited

U.S. PATENT DOCUMENTS

| | | | | |
|---|---|---|---|---|
| 2,672,143 A | * | 3/1954 | Gold et al. ............ | 433/80 |
| 3,735,491 A | * | 5/1973 | Pabalan, Jr. ............ | 433/93 |
| 3,753,292 A | * | 8/1973 | Hutson ............ | 433/96 |
| 4,260,378 A | * | 4/1981 | O'Neil ............ | 433/93 |
| 5,071,347 A | * | 12/1991 | McGuire ............ | 433/91 |
| 5,295,830 A | * | 3/1994 | Shen et al. ............ | 433/116 |
| 5,322,521 A | * | 6/1994 | Wilk ............ | 604/317 |
| 5,460,524 A | * | 10/1995 | Anderson ............ | 433/93 |
| 5,725,374 A | * | 3/1998 | Young ............ | 433/95 |
| 5,873,718 A | * | 2/1999 | Sullivan ............ | 433/93 |
| 5,882,194 A | * | 3/1999 | Davis et al. ............ | 433/29 |
| 5,924,866 A | * | 7/1999 | Eldreth ............ | 433/140 |

FOREIGN PATENT DOCUMENTS

| | | |
|---|---|---|
| JP | 7-204215 | 8/1995 |
| JP | 11-028219 | 2/1999 |

* cited by examiner

*Primary Examiner*—Melba N. Bumgarner
*Assistant Examiner*—Jonathan Werner
(74) *Attorney, Agent, or Firm*—Wenderoth, Lind & Ponack, L.L.P.

(57) ABSTRACT

A dental suction device includes a hollow tube having both flexibility and shape retainability. The tube has its both ends connected to a connector and is formed with suction holes. The connector can be connected to a vacuum source. A suction force produced by the vacuum source can thus be applied to the suction holes of the tube through a passage formed in the connector. The connector includes a valve for adjusting the degree of opening of the passage formed in the connector and thus the suction force applied to the suction holes. The valve includes a valve body mounted in the connector and a manual lever for controlling the valve body.

4 Claims, 6 Drawing Sheets

DENTAL SUCTION DEVICE

BACKGROUND OF THE INVENTION

This invention relates to a suction device for use in dental treatment and which can reliably suck saliva, blood and liquid drugs in the mouth of a patient during dental treatment and can simultaneously control the temperature and humidity in the mouth.

A conventional such suction device has a nozzle at the tip of a suction pipe. The nozzle is inserted into the mouth of a patient to suck up saliva and blood in the mouth through the nozzle. In order to effectively suck saliva and blood, the nozzle has to be moved sufficiently close to the area where the treatment is being carried out. It is difficult for one person to carry out such a delicate operation during dental treatment.

Thus, instead of the dentist, an assistant operates the suction device while the dentist is performing dental treatment. But in such a case, the assistant has to keep the nozzle of the suction device sufficiently apart from the area being treated in the mouth so as not to interfere with the dental treatment performed by the dentist. Therefore, no sufficient suction force can be applied to the area being treated.

When using a dental adhesive in the mouth of a patient, it is necessary to keep the temperature and humidity in the mouth sufficiently low in order to obtain sufficiently high bond strength. But the temperature in the mouth is usually as high as the body temperature and the humidity in the mouth is nearly 100%. Thus, in order for a dental adhesive to show sufficient bond strength in the mouth, it is necessary to lower the temperature and humidity in an area where the adhesive is used by sucking air in this area. But as described above, it was difficult to apply sufficient suction force to the area where dental treatment is being performed.

In (unexamined) JP patent publications 7-204215 and 11-28219, we proposed a dental suction device comprising a hollow tube having flexibility and shape retainability and formed with suction holes, and a connector having a vacuum port which can be connected to a vacuum source and connected to one or both ends of the tube.

Because the tube is flexible and has shape retainability, it can be positioned in the mouth so that the suction holes are located close to a tooth to be treated. Once set in position in the mouth, it is not necessary to keep holding the tube with a hand. Thus, sufficient suction force can be applied to a desired area in the mouth.

But this suction device has no means for adjusting the suction force in a delicate manner. Particularly, it is possible only to turn on or off the vacuum source. Thus, it was impossible to adjust the temperature and humidity in the mouth freely to any desired level.

For example, it was impossible to increase the temperature in the mouth to a level at which the efficacy of drugs such as hypochlorite, phosphate or ETDA is the highest when they are applied to teeth, gum or mucous membranes.

Cements are used to bond crowns, inlays and bridges to teeth. These dental cements harden more quickly at elevated temperatures. Thus, if it takes a long time for treatment, the dentist may desire to delay the hardening of a cement. When the treatment has finished, the dentist will now desire to harden the cement as quickly as possible. But this is of course impossible with conventional dental suction devices as disclosed in the abovementioned publications because the suction force cannot be controlled at all.

An object of the present invention is to provide a dental suction device of the above-described type having means which enables a dental practitioner to delicately control the suction force produced in the flexible, hollow tube so that he can adjust the temperature and humidity in the mouth of a patient by controlling the suction force produced in the tube while performing dental treatment.

SUMMARY OF THE INVENTION

According to this invention, there is provided a dental suction device comprising a hollow tube having flexibility and shape retainability, the tube being formed with suction holes and having two ends, a connector connected to at least one of the two ends of the tube and having a vacuum port adapted to be connected to a vacuum source, the connector having a passage through which the vacuum port communicates with the at least one of the two ends of the tube, and a valve mounted in the connector for adjusting the degree of opening of the passage.

The dental suction device may further comprise an additional flexible tube having one of two ends thereof connected to the connector and carrying a suction needle at the other end thereof, the passage communicating with the one of the two ends of the additional flexible tube.

The connector preferably comprises a first member to which is connected the vacuum port and a second member to which are connected the at least one of the two ends of the tube and/or the one of the two ends of the additional tube, the second member being coupled to the first member so as to be rotatable relative to the first member. Preferably, the passage extends through the first and second members, and the valve is mounted in the first member with the second member rotatable about the axis of the passage relative to the first member. Further preferably, the first member is formed with a cylindrical hole extending substantially perpendicular to the passage, the valve comprising a cylindrical member airtightly and rotatably received in the cylindrical hole and formed with a valve hole extending therethrough in a diametric direction of the cylindrical member, the valve hole being arranged so as to align with the passage when the cylindrical member is in a first predetermined angular position relative to the first member and to be completely out of communication with the passage when the cylindrical member is in a second predetermined angular position relative to the first member. The valve further comprises a lever for rotating the cylindrical member, the lever being moveable between a first position where the cylindrical member is in the first predetermined angular position and a second position where the cylindrical member is in the second predetermined angular position. Preferably, the dental suction device further comprises a spacer provided at a portion of the tube remote from the connector and adapted to be disposed between two objects to keep the two objects spaced from each other.

According to this invention, a dentist can freely adjust the section force produced in the tube, thereby controlling the temperature and humidity in the mouth of a patient by operating the lever of the valve. It is also possible to freely adjust the temperature and humidity in a root canal wall by inserting the suction needle into the root canal.

By turning the first member of the connector relative to the second member, the lever can be oriented to any desired position where the dentist can operate the lever easily with one hand while holding a dental tool with the other hand.

BRIEF DESCRIPTION OF THE DRAWINGS

Other features and objects of the present invention will become apparent from the following description made with reference to the accompanying drawings.

DETAILED DESCRIPTION OF THE PREFERRED EMBODIMENTS

Figure 1:
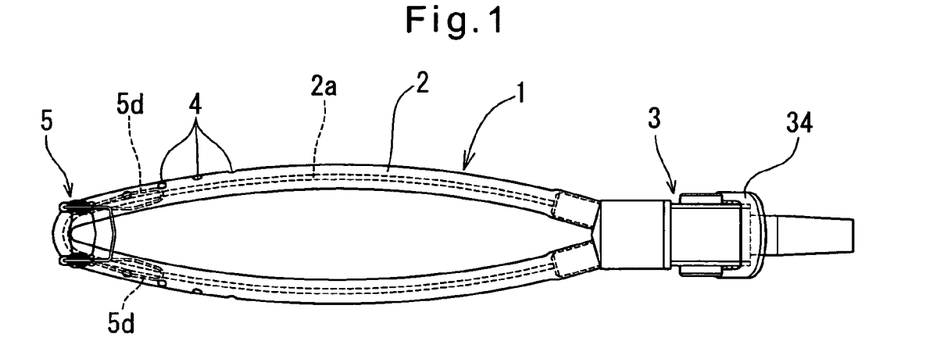
FIG. 1 is a plan view of a dental suction device of a first embodiment according to the present invention.
Figure 2:
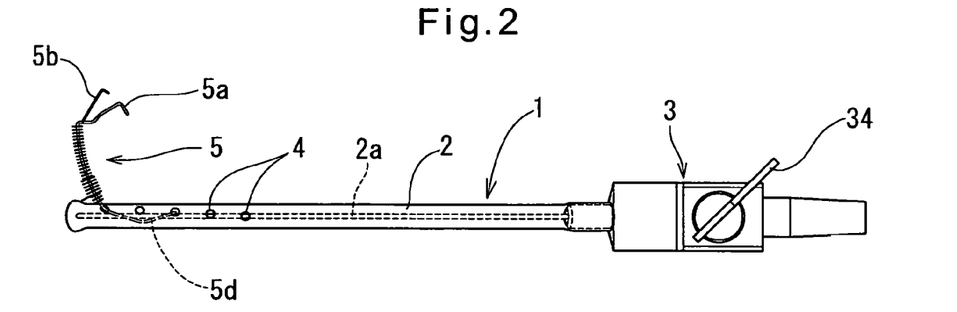
FIG. 2 is a side view of the same.
Figure 14:
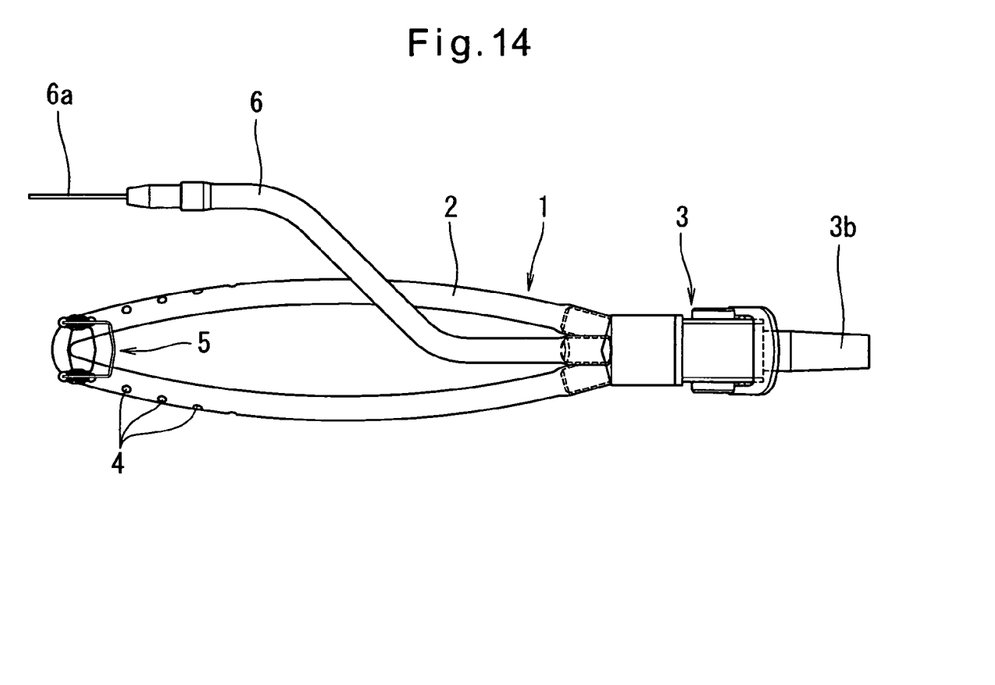
FIG. 14 is a plan view of a dental suction device of a third embodiment according to the present invention.
Figure 15:
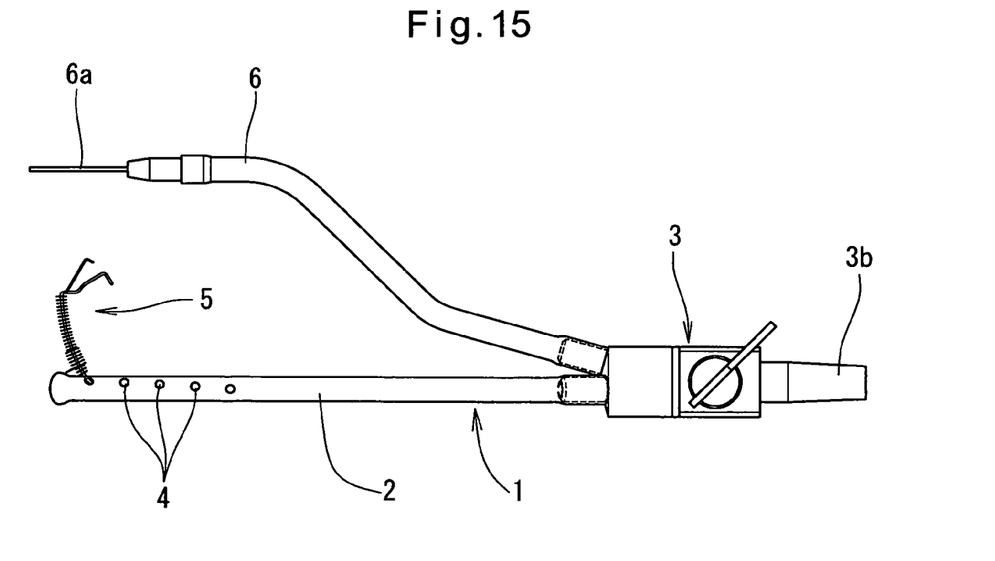
FIG. 15 is a side view of the same.

Now referring to the drawings, first FIGS. 1 and 2, the dental suction device 1 according to the invention comprises a flexible, hollow, looped tube 2 having shape retainability, a connector 3 connected to the tube 2, and a spacer 5 mounted on the tube 2 at its front end. As shown in FIGS. 14 and 15, an additional tube 6 carrying a hollow suction needle 6a at its front end may be connected to the connector 3.

In order that the tube 2, which is made of a soft material such as rubber or a synthetic resin, maintains flexibility and shape retainability, a flexible wire 2a having shape retainability such as a copper, aluminum or silver wire is inserted in the tube 2. The wire 2a makes it possible for the tube 2 to be shaped such that it can be brought into close contact with a line of teeth of a patient.

The wire 2a does not necessarily have to be provided over the entire length of the tube 2. For example, it may be provided only where the tube 2 is bent. In this case, the tube 2 has shape retainability only at its bent portion.

Figure 3:
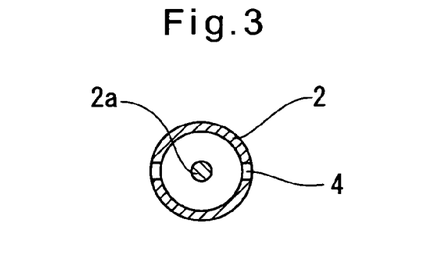
FIG. 3 is a sectional view of a hollow tube of the dental suction device of FIG. 1.
Figure 4:
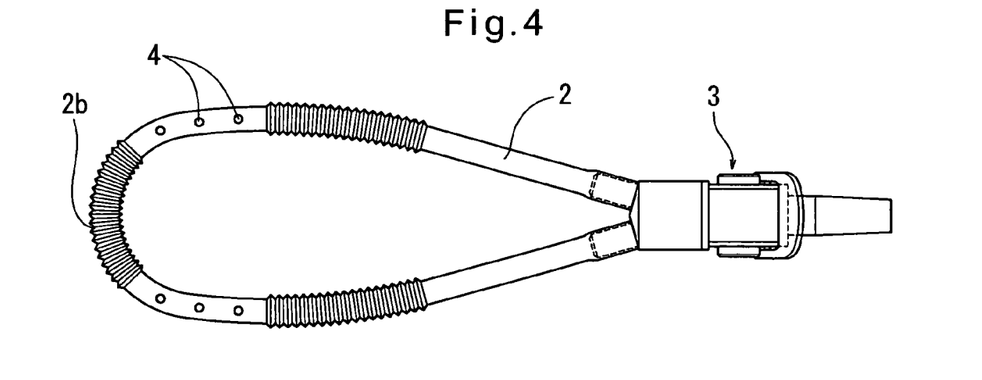
FIG. 4 is a plan view of a dental suction device of a second embodiment according to the present invention.

Another means for imparting shape retainability to the tube 2 is shown in FIG. 4, in which the tube 2 is formed of a semi-hard synthetic resin and fine bellows 2b are formed over the entire length of the tube or only at its bent portion or portions. In this arrangement, too, the wire 2a shown in FIGS. 1-3 may be inserted in the tube 2, or instead of the wire 2a, a helical spring may be inserted in the tube 2 so that its pitch will be equal to the pitch of the bellows 2b.

Figure 5:
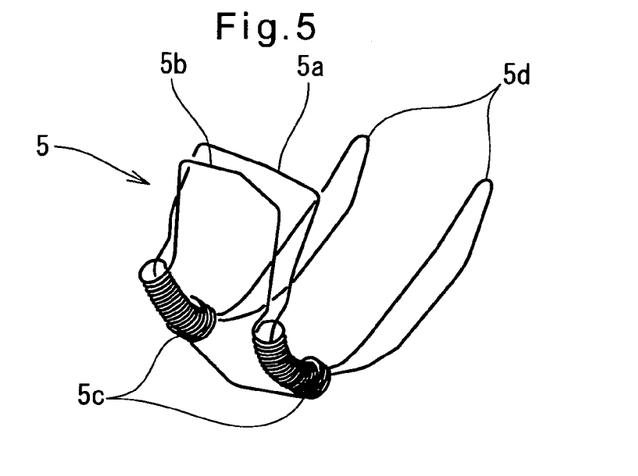
FIG. 5 is a perspective view of a spacer.

The spacer 5 comprises, as shown in FIG. 5, two parallel, helical coil portions 5c, legs 5d extending from the lower ends of the coil portions 5c and inserted in the tube 2, thereby positioning the coil portions 5c relative to the tube 2, a U-shaped stopper 5a having its ends connected to the respective upper ends of the coil portions 5c, and a U-shaped abutment 5b having its ends supported by the coil portions 5c at their upper ends so as to be elastically pivotable about its ends toward and away from the stopper 5a.

Figure 13:
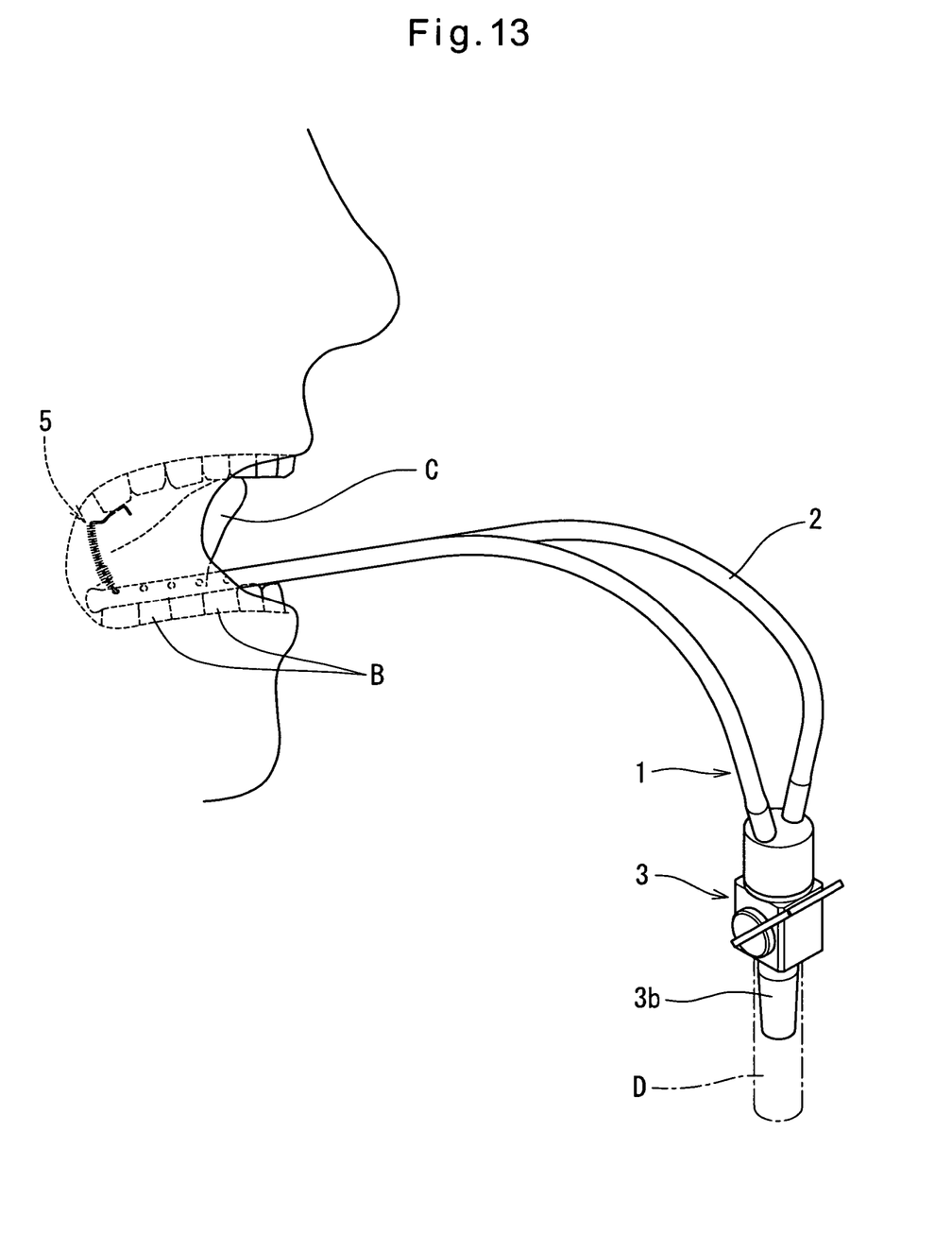

These elements of the spacer 5 are arranged such that with the front end of the looped tube 2 set in position at or near a tooth of a patient being treated, the abutment 5b abuts and elastically supports the tooth that opposes the tooth to be treated when the patient is opening the mouth. Thus in this state, the spacer 5 helps the patient keep his or her mouth open while the affected tooth is being treated as shown in FIG. 13.

Figure 6:
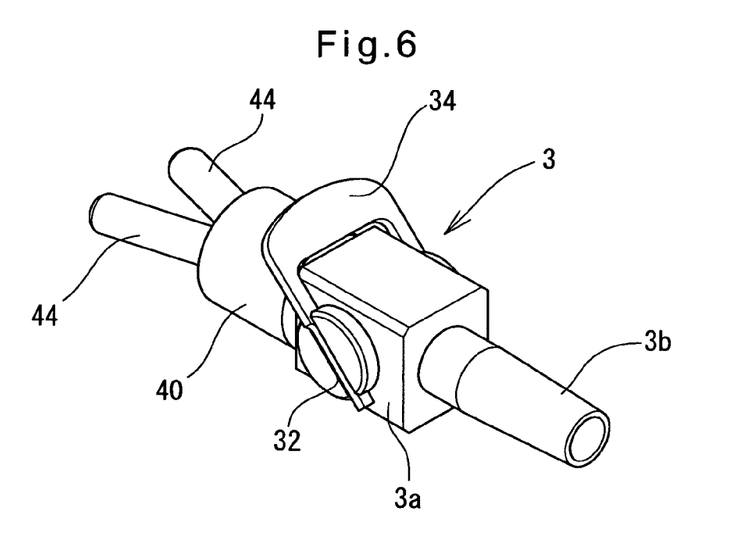
FIG. 6 is a perspective view of a connector.
Figure 7:
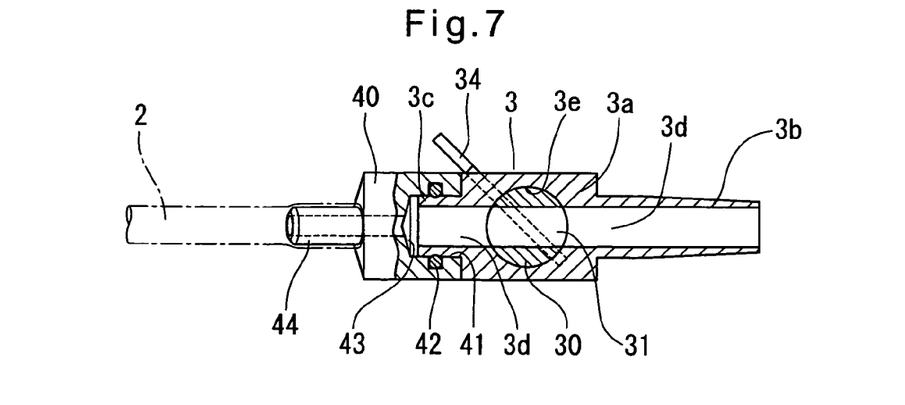
FIG. 7 is a longitudinal sectional view of the connector.

Now referring to FIGS. 6 and 7, the connector 3 includes a box-shaped body 3a formed with a vacuum port 3b on one side thereof and a mounting protrusion 3c on the opposite side thereof. A rotary member 40 having tube-connecting projections 44 is rotatably mounted on the mounting protrusion 3c. A straight passage 3d is formed through the vacuum port 3b, the body 3a and the mounting protrusion 3c.

Figure 8:
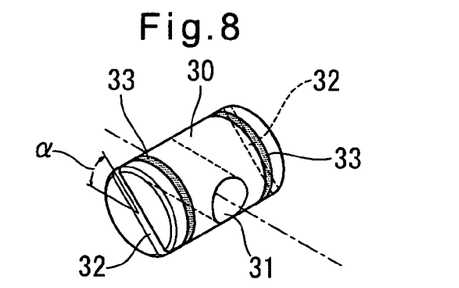
FIG. 8 is a perspective view of a valve body to be mounted in the connector.

A horizontal hole 3e having a greater diameter than the passage 3d extends through the body 3a so as to cross the passage 3d at a right angle thereto. A cylindrical valve body 30 as shown in FIG. 8 is airtightly and rotatably received in the hole 3e. The valve body 30 has a through valve hole 31 having substantially the same diameter as the passage 3d and extending in a direction perpendicular to the axis of the valve body 30 so as to align with the passage 3d when the valve body 30 is at a predetermined angular position. Thus, by rotating the valve body 30, it is possible to adjust the flow rate of a fluid that flows through the passage 3d.

Figure 9:
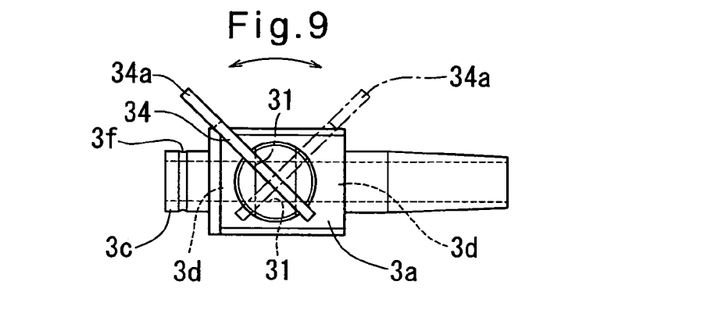
FIG. 9 is a longitudinal sectional view of the valve body and a lever.

In each of the end faces of the valve body 30, a groove 32 is formed that is inclined at an angle $\alpha$=approximately 45 degrees with respect to the axis of the valve hole 31. The end portions of the valve body 30 where there exist the grooves 32 protrude from the side walls of the body 3a. The valve body 30 carries seal rings 33 at its portions near its ends but inside the hole 3e. A U-shaped lever 34 has its legs received in the respective grooves 32 and fixed to the valve body 30 with e.g. screws. By pushing or pulling the crossbar portion 34a of the U-shaped lever 34, the valve body 30 can be turned to adjust the degree of opening of the valve hole 31. Preferably, the crossbar portion 34a of the lever 34 is arranged so as to abut the top wall of the body 3a when the lever 34 is pivoted by 45 degrees in either direction from the vertical position as shown in FIG. 9. With this arrangement, because the grooves 32 are inclined at an angle of 45 degrees with respect to the axis of the valve hole 31, the valve hole 31 fully opens (i.e. aligns with the passage 3d) when the crossbar portion 34a is in abutment with the top wall of the body 3a by pivoting the lever 34 in one direction (e.g. clockwise), and will be fully closed when the crossbar portion 34a is in abutment with the top wall of the body 3a by pivoting the lever 34 in the opposite direction (e.g. counterclockwise). Thus, simply by pivoting the lever 34, either clockwise or counterclockwise, all the way until the crossbar portion 34a abuts the top wall of the body 3a with one hand, the valve hole 31 can be fully opened or fully closed.

Figure 10:
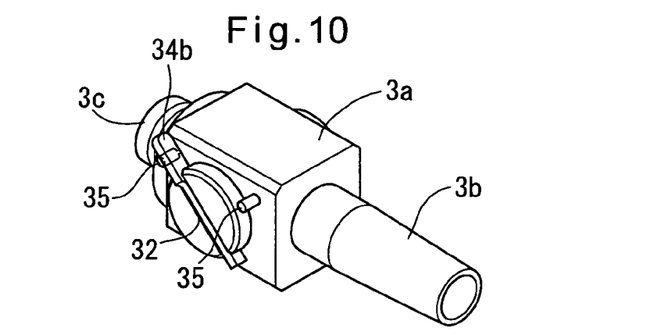
FIG. 10 is a perspective view of a different connector body.

Instead of the U-shaped lever 34, a bar-shaped lever 34b as shown in FIG. 10 may be used. This lever is received in the groove 32 formed in one end face of the valve body 30. Thus, in this arrangement, the groove 32 at the other end of the valve body 30 is not necessary and may be omitted. At positions corresponding to the fully open position and fully closed position of the valve hole 31, the lever 34b is adapted to abut and engage stoppers 35.

Figure 11:
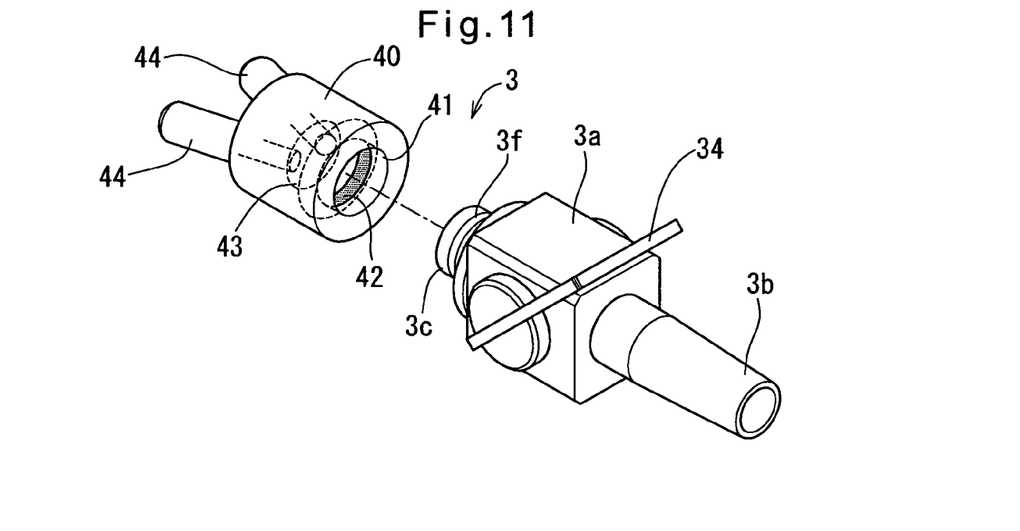
FIG. 11 is an exploded perspective view of the connector of FIG. 1.

As shown in FIGS. 7 and 11, the rotary member 40 is rotatable about the axis of the mounting protrusion 3c. The rotary member 40 is preferably a cylindrical member formed with a recess 41 in one end face opposite the end face on which are provided the tube-connecting projections 44. The rotary member 40 is mounted on the mounting protrusion 3*c* by pressing the protrusion 3*c* into the recess 41. The mounting protrusion 3*c* is formed with an annular groove 3*f* in its outer periphery near its front end. An elastic seal ring 42 is fitted in the inner wall of the recess 41. The groove 3*f* and the seal ring 42 are arranged such that the latter engages in the former when the mounting protrusion 3*c* is fully pressed into the recess 41. With the seal ring 42 engaged in the groove 3*f*, the seal ring 42 also serves to prevent the member 40 from coming off the mounting protrusion 3*c*. In a known manner, the seal ring 42 has lubricity to ensure smooth rotation of the rotary member 40. The rotary member 40 is formed with a passage 43 through which the passage 3*d* communicates with the interior of the tube-connecting projections 44.

Figure 12:
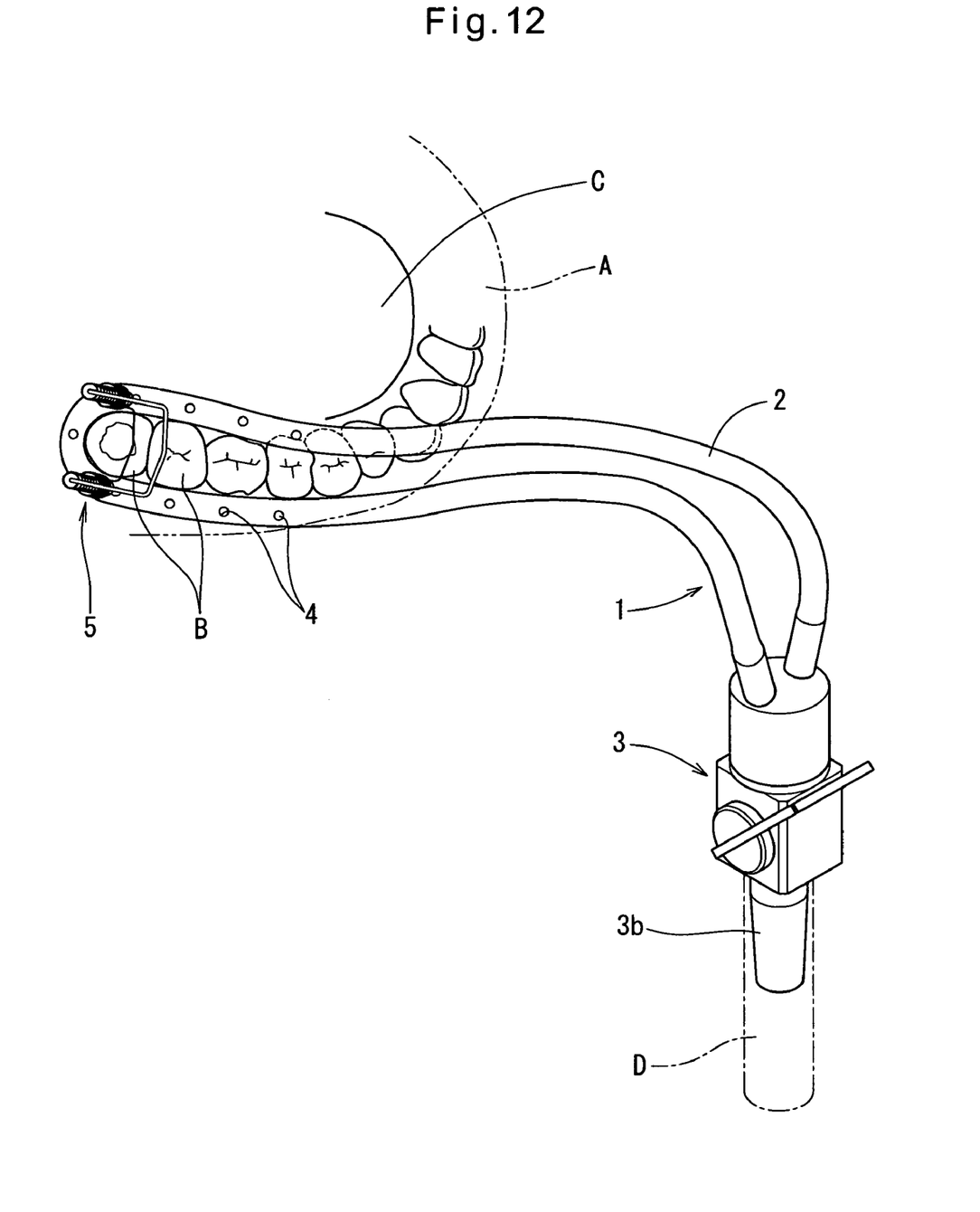
FIGS. 12 and 13 show how the dental suction device of FIG. 1 is used in the mouth of a patient during dental treatment.

Description is now made of how the dental suction device 1 is used, with reference to FIGS. 12 and 13.

A dentist shapes the tube 2 so as to correspond to the contours of a tooth to be treated and adjacent teeth of a patient, and inserts the tube 2 into the mouth of the patient so as to be in close contact with these teeth.

With the abutment 5*b* of the spacer 5 in abutment with the tooth opposing the tooth to be treated, the patient lightly bites the spacer 5 to stably hold the tube 2 in position. The elastic force of the spacer 5 makes it easier for the patient to keep his or her mouth open during treatment.

The dentist bends the portion of the tube 2 that is out of the mouth so that the tube will not interfere with the treatment, connects the vacuum port 3*b* of the connector 3 to hose D leading to a vacuum source, and activates the vacuum source to suck saliva and other fluids in the mouth through suction holes 4 formed in the tube 2.

The dentist can freely adjust the suction force simply by moving the lever 34 with one hand to adjust the temperature and humidity in the mouth. For example, when a dental adhesive is used in the mouth, the dentist moves the lever 34 so as to open the valve hole 31 relatively widely to reduce the humidity and temperature in the mouth. This is because a dental adhesive shows higher adhesion strength at a lower humidity and temperature.

When applying hypochlorite, phosphate or ETDA to teeth, gums or a mucous membrane, it is necessary to increase the temperature in the mouth for higher efficacy of these drugs. Thus, the dentist moves the lever 34 to reduce the suction force, and thereby to increase the temperature in the mouth as close to the body temperature as possible.

Cements are used to bond crowns, inlays and bridges to teeth. These dental cements harden more quickly at elevated temperatures. Thus, if it takes a long time for treatment, the dentist may desire to delay the hardening of a cement. In such a case, he can decrease the temperature in the mouth by controlling the suction force of the suction device in the above-described manner. When the treatment has finished, the dentist will now desire to harden the cement as quickly as possible. Thus, he closes the valve hole 31 by moving the lever 34 to increase the temperature in the mouth and thus to quicken hardening of the cement.

Because the rotary member 40 and the body 3*a* of the connector are rotatable relative to each other, the dentist can turn the body 3*a* to a position where the lever 34 can be most easily operated even while the tube 2 is stuck in the mouth of a patient.

During treatment, the tube 2 restricts free movement of the tongue C. Thus, while working on teeth B with a dental cutting tool, the tongue C, lips and mucous membranes are less likely to be damaged by the cutting tool.

As shown in FIGS. 14 and 15, the additional tube 6 may be connected to the connector 3. This tube has the suction needle 6*a* at its free end. It has to be flexible but may not have shape retainability. The needle 6*a* is stuck into a root canal to dry the root canal wall when treating the root canal. While not in use, the tube 6 may be just left dangling from the connector. But preferably, the tube 6 is provided with a clip near its free end so that the tube 6 can be bent and clipped on the connector while not in use. Further preferably, the needle 6*a* is detachable from the tube 6 so that while not in use, the needle 6*a* can be replaced with a cap. With this arrangement, while the tube 6 is not used, its opening can be sealed with the cap. This prevents a loss of vacuum power.

What is claimed is:

1. A dental suction device comprising:

a hollow tube having flexibility and shape retainability, said tube being formed with suction holes and having two ends;

a connector connected to at least one of said two ends of said tube and having a vacuum port adapted to be connected to a vacuum source, said connector having a passage through which said vacuum port communicates with said at least one of the two ends of said tube; and a valve mounted in said connector for adjusting a degree of opening of said passage;

wherein said connector comprises a first member to which is connected said vacuum port and a second member to which is connected said at least one of the two ends of said tube, said second member being coupled to said first member so as to be rotatable relative to said first member;

wherein said passage extends through said first and second members;

wherein said valve is mounted in said first member;

wherein said second member is rotatable about an axis of said passage relative to said first member;

wherein one of said first and second members includes a cylindrical mounting protrusion having an outer cylindrical surface with an annular groove formed therein, said passage extending through said cylindrical mounting protrusion;

wherein the other of said first and second members has a cylindrical bore formed at one end thereof, said cylindrical bore having an inner surface;

wherein a seal ring, which is separate and discrete from said other of said first and second members, is secured to said inner surface of said cylindrical bore of said other of said first and second members; and wherein said cylindrical mounting protrusion is rotatably mounted in said cylindrical bore and said seal ring is provided with lubricity and is engaged in said annular groove of said cylindrical mounting protrusion in such a manner as to allow relative rotation between said first and second members.

2. A dental suction device comprising:

a hollow tube having flexibility and shape retainability, said tube being formed with suction holes and having two ends;

a connector connected to at least one of said two ends of said tube and having a vacuum port adapted to be connected to a vacuum source, said connector having a passage through which said vacuum port communicates with said at least one of the two ends of said tube;

a valve mounted in said connector for adjusting a degree of opening of said passage;

an additional flexible tube having one of two ends thereof connected to said connector and carrying a suction needle at the other end thereof, said passage communicating with said one of the two ends of said additional flexible tube;

wherein said connector comprises a first member to which is connected said vacuum port and a second member to which are connected said at least one of the two ends of said tube and said one of the two ends of said additional tube, said second member being coupled to said first member so as to be rotatable relative to said first member;

wherein said passage extends through said first and second members;

wherein said valve is mounted in said first member;

wherein said second member is rotatable about an axis of said passage relative to said first member;

wherein one of said first and second members includes a cylindrical mounting protrusion having an outer cylindrical surface with an annular groove formed therein, said passage extending through said cylindrical mounting protrusion;

wherein the other of said first and second members has a cylindrical bore formed at one end thereof, said cylindrical bore having an inner surface;

wherein a seal ring, which is separate and discrete from said other of said first and second members, is secured to said inner surface of said cylindrical bore of said other of said first and second members; and wherein said cylindrical mounting protrusion is rotatably mounted in said cylindrical bore and said seal ring is provided with lubricity and is engaged in said annular groove of said cylindrical mounting protrusion in such a manner as to allow relative rotation between said first and second members.

3. A dental suction device comprising:

a hollow tube having flexibility and shape retainability, said tube being formed with suction holes and having two ends;

a connector connected to at least one of said two ends of said tube and having a vacuum port adapted to be connected to a vacuum source, said connector having a passage through which said vacuum port communicates with said at least one of the two ends of said tube; and a valve mounted in said connector for adjusting a degree of opening of said passage;

wherein said connector comprises a first member to which is connected said vacuum port and a second member to which is connected said at least one of the two ends of said tube, said second member being coupled to said first member so as to be rotatable relative to said first member;

wherein said passage extends through said first and second members;

wherein said valve is mounted in said first member;

wherein said second member is rotatable about an axis of said passage relative to said first member;

wherein said first member is formed with a cylindrical hole extending substantially perpendicular to said passage, said valve comprising a cylindrical member airtightly and rotatably received in said cylindrical hole and formed with a valve hole extending therethrough in a diametric direction of said cylindrical member, said valve hole being arranged so as to align with said passage when said cylindrical member is in a first predetermined angular position relative to said first member and to be completely out of communication with said passage when said cylindrical member is in a second predetermined angular position relative to said first member;

wherein said valve further comprises a lever for rotating said cylindrical member, said lever being moveable between a first position in which said cylindrical member is in said first predetermined angular position and a second position in which said cylindrical member is in said second predetermined angular position;

wherein said lever includes at least one elongated arm having a longitudinal center axis, said arm being secured to said cylindrical member such that said longitudinal center axis of said arm forms an angle of approximately 45 degrees with respect to an axis of said valve hole formed in said cylindrical member; and wherein said first member is provided with stoppers arranged to abut said elongated arm at said first and second positions in order to align said valve hole relative to said passage in said first and second predetermined angular positions of said cylindrical member.

4. A dental suction device comprising:

a hollow tube having flexibility and shape retainability, said tube being formed with suction holes and having two ends;

a connector connected to at least one of said two ends of said tube and having a vacuum port adapted to be connected to a vacuum source, said connector having a passage through which said vacuum port communicates with said at least one of the two ends of said tube;

a valve mounted in said connector for adjusting a degree of opening of said passage;

an additional flexible tube having one of two ends thereof connected to said connector and carrying a suction needle at the other end thereof, said passage communicating with said one of the two ends of said additional flexible tube;

wherein said connector comprises a first member to which is connected said vacuum port and a second member to which are connected said at least one of the two ends of said tube and said one of the two ends of said additional tube, said second member being coupled to said first member so as to be rotatable relative to said first member;

wherein said passage extends through said first and second members;

wherein said valve is mounted in said first member;

wherein said second member is rotatable about an axis of said passage relative to said first member;

wherein said first member is formed with a cylindrical hole extending substantially perpendicular to said passage, said valve comprising a cylindrical member airtightly and rotatably received in said cylindrical hole and formed with a valve hole extending therethrough in a diametric direction of said cylindrical member, said valve hole being arranged so as to align with said passage when said cylindrical member is in a first predetermined angular position relative to said first member and to be completely out of communication with said passage when said cylindrical member is in a second predetermined angular position relative to said first member;

wherein said valve further comprises a lever for rotating said cylindrical member, said lever being moveable between a first position in which said cylindrical member is in said first predetermined angular position and a second position in which said cylindrical member is in said second predetermined angular position; and wherein said lever includes at least one elongated arm having a longitudinal center axis, said arm being secured to said cylindrical member such that said longitudinal center axis of said arm forms an angle of approximately 45 degrees with respect to an axis of said valve hole formed in said cylindrical member; and wherein said first member is provided with stoppers arranged to abut said elongated arm at said first and second positions in order to align said valve hole relative to said passage in said first and second predetermined angular positions of said cylindrical member.

* * * * *